United States Patent [19]

Dürr et al.

[11] 4,162,221
[45] Jul. 24, 1979

[54] SYNTHETIC MUSK-BASED COMPOSITION, ITS PRODUCTION AND APPLICATIONS

[75] Inventors: Louis Dürr, Paris; Francis Legrand, Mulhouse, both of France

[73] Assignee: Societe des Produits Chimiques et Matieres Colorantes de Mulhouse, Paris, France

[21] Appl. No.: 872,756

[22] Filed: Jan. 27, 1978

[30] Foreign Application Priority Data

Jan. 31, 1977 [FR] France .................................. 77 02663

[51] Int. Cl.² ........................... C11B 9/00; C11D 3/50
[52] U.S. Cl. ........................................ 252/1; 252/522; 424/176; 424/349
[58] Field of Search .................. 252/1, 522, 134, 174, 252/89 R; 260/645; 424/176, 349

[56] References Cited

U.S. PATENT DOCUMENTS 2,377,727  6/1945  Teahan ................................. 260/645
3,705,158  12/1972  Pittet et al. ........................... 252/522

*Primary Examiner*—Leland A. Sebastian
*Attorney, Agent, or Firm*—Berman, Aisenberg & Platt

[57] ABSTRACT

The composition based on nitrated synthetic musk, contains about 0.5 to 50% by weight with respect to the total composition, of a modifying agent, the complement to 100% being constituted by the nitrated synthetic musk. The modifying agent is a solid non-film-former, at least partially soluble in lower alcohols and being in addition odorless and non-toxic or non-irritant in contact with human tissue. It is specially useful in the perfumery, washing materials and detergent industries.

28 Claims, No Drawings

SYNTHETIC MUSK-BASED COMPOSITION, ITS PRODUCTION AND APPLICATIONS

BACKGROUND OF THE INVENTION

1. Field of the Invention

The invention relates to the field of synthetic musks, and more particularly that of nitrated synthetic musks. More particularly again, the invention relates to a novel composition based on nitrated synthetic musks, which has a special advantage in its application to the industries of perfumery, washing materials and detergents.

2. Description of the Prior Art

To the man skilled in the art, nitrated synthetic musks are known and their use incorporated into products derived from the industry of perfumes, washing materials and the like. Among the nitrated synthetic musks most frequently encountered in practice are: musk xylene, musk ambrette, musk ketone, musk tibetene and musk moskene.

The exact chemical names of these musks are as follows:

Musk xylene
  1-t. butyl-3,5-dimethyl-2,4,6-trinitrobenzene
Musk ketone
  4-t. butyl-2-methyl-3,6-dinitro-acetophenone
Musk ambrette
  6-t. butyl-3-methyl-2,4-dinitro anisole
Musk tibetene
  2,6-dinitro-3,4,5-trimethyl-tert-butylbenzene
Musk moskene
  1,1,3,3,5-pentamethyl-4,6-dinitroindane.

The musks concerned are products which have been known for a long time. They are described respectively in the patents:

Musk xylene: Patents FR 194,833; GB 18,521; DT 77,299
  Musk ambrette: DT 62,362
  Musk ketone: DT 87,130
  Musk moskene: US 1,892,128
  Musk tibetene: US 2,072,293

It is noted in practice that there are certain difficulties in the formulation of musk-based compositions, particularly when it is desired to mix the musk with intended additives, for example, to ensure complete stability thereof. The musk-based compositions are then difficult to introduce into the usual formulations of perfumery, which naturally presents practical drawbacks.

In addition, certain recent works have considered that synthetic musks, for the very reason of the presence of nitrated substituents, were capable of constituting dangers, although no veritable observation has been made on the claimed explosive properties of the nitrated synthetic musks concerned; for example, musk xylene, which is a trinitro derivative of tertiary butyl-m-xylene, does not possess proper explosive properties; this must be attributable to its chemical structure and, notably, to the presence of two methyl substituent groups and of a tertiary butyl group on the benzene ring. According to results of these works, musk xylene would be catalogued in the so-called dangerous category IA, failing moreover the existence of a suitable category, in referring to international transportation regulations normally in force.

On the other hand it should be noted that, according to prior art, there has already been proposed the use, in fragrance compositions, of certain additives to obtain fragrance compositions having particular properties.

For this purpose reference may be made to the U.S. Pat. No. 3,939,099 which relates to fragrance compositions whose initial odor strength is adequate when said composition is applied to a substrate, for example the skin and which remains noticeable for a long period of time. These compositions comprise a fragrance oil and a filmforming agent, these constituents being mutually soluble in a water-ethanol solvent system, which represents the third constituent of this composition. In general the fragrance oil is present in this composition in an amount comprised between 0.01 and 50.0% by weight, the filmforming agent in an amount comprised between 0.01 and 20.0% by weight and the solvent in an amount comprised between 30.0 and 99.98% by weight, all the percentages indicated being calculated with respect to the total weight of the composition. Among suitable fragrance oils are included musk ketone and musk ambrette. The filmforming agents are ionic or non-ionic derivatives of water-soluble polymers, for example derivatives of polyvinylpyrrolidone and derivatives of cellulose. It seems that in this composition, the fragrance oil is entrapped by the filmforming agent in the course of evaporation of the volatile solvent and that the release of said fragrance oil thus takes place at a reduced release rate.

Great Britain Pat. No. 716,882 relates to a process for the production of water-soluble powdered perfurmed products. This process consists of taking a water-soluble substance dissolving it in water, drying it by spraying the resultant solution to obtain a water-soluble vehicle and absorbing in said vehicle at least 10 percent, with respect to its own weight, of the perfume. Thus this patent relates to perfumed products which are pulverulent and soluble in water and which contain, by way of additive, a vehicle conferring on them particular properties.

French Pat. No. 1,034,444 relates to a dry solid perfume which contains, by way of supporting substance for the essences, a polyvinyl alcohol. The dry perfumes thus obtained do not lose their aroma even after considerable time. The polyvinyl alcohol enables the volatility of the essences to be reduced; it is indicated in this patent that other organic substances containing the hydroxyl radical and of high molecular weight, such as cellulose, starch and lactose, are not suitable.

French Pat. No. 1,238,722 relates to a process for obtaining solidified perfumes which consist of dispersions of alkali stearates in non-miscible solvents or in essential perfumes or a mixture of the two. The additive applied in this process, namely: the alkali stearate, enables the production of solidified perfumes.

It is an object of the present invention to provide a nitrated synthetic musk-based composition which is completely free of the aforesaid drawbacks.

It is another object of the invention to provide a novel composition which can be easily formulated within a product of perfumery, a detergent or a washing material, whilst having the same olfactory properties as the basic musk.

It is another object of the invention to provide a novel synthetic musk composition which possesses stability enabling it to be considered as belonging to the category of normal products.

It is an another object of the invention to provide an industrial product, such as perfume, detergent or washing agent, comprising a nitrated synthetic musk-based composition.

GENERAL DESCRIPTION OF THE INVENTION

Accordingly, the present invention relates to a nitrated synthetic musk composition which is suitable as a useful ingredient for the preparation of fragrance compositions. It is characterized by the fact that it contains, as an additive a modifying agent in defined amounts.

The composition (according to the invention) based on nitrated synthetic musk is characterized in that it contains about 0.5 to 50%, in particular about 2 to 20%, and preferably from about 5 to 10% by weight (with respect to the total composition), of a modifying agent, the complement to 100% being constituted by nitrated synthetic musk.

In the present specification, the expression "modifying agent" denotes a non-filmforming solid product, at least partially soluble in lower alcohols, such as ethyl alcohol or isopropyl alcohol, said product being, in addition, odorless and not being either toxic or irritant when it is in contact with human tissue.

According to an essential characteristic of the invention, the modifying agent is a solid product which does not change substantially the physical form of the base musk. The novel composition is hence presented in the form of an extremely intimate mixture of constituents which is particularly well adapted to formulation in producing perfumery, detergent and washing materials since the modifying agent, while rendering optimal the stability of the musk, does not interfere with the physical and olfactory properties of the latter. In this regard, it is to be noted that a composition based on musk-containing stabilizers of the alkyl phthalate type is in the form of a sticky substance.

Another important characteristic of the modifying agent is its solubility in lower alcohols. Although not obligatory, it is also advantageous for the modifying agent to be at least partially soluble in water.

According to another feature, the modifying agent must be practically free of odor. Moreover, it must be neither toxic nor irritant with respect to human tissues, in a way it must have the character of a food additive.

In addition the modifying agent must be non-filmforming. It is thought in fact that the use of a filmforming agent could cause problems of compatibility in using the thus-modified musk in a perfume composition.

The modifying agent may be selected by the man skilled in the art from a certain number of classes of compounds, taking into account the preceding indications. The preferred class is represented by compounds of the category of sugars, such as maltose, saccharose, glucose, lactose, sucrose and other similar sugars, as well as their ethers and esters. Among these, saccharose, maltose, glucose and lactose are successfully used.

Other possible categories are solid hydroxylated products of the type of polyols, such as pentaerythritol and mannitol, paraffins or solid deodorized hydrocarbons.

As has been mentioned, the modifying agent must not interfere with the properties of the base musk, and this is why there is no practical advantage in using, within the composition, a higher amount than approximately 50% by weight with respect to the total weight of the composition. The lower limit of the amount of modifying agent is not critical. It is simply necessary that it be sufficient to ensure optimal stability of the musk. As a general rule, an amount greater than 0.5% is suitable.

The preferred range of modifying agent is comprised between about 5 and 10% of the weight of the total composition.

In the composition according to the invention, it is possible to use any of the nitrated synthetic musks whose references have been given at the beginning of the present specification. Advantageously musk xylene, musk ketone and musk ambrette are used. It will be recalled here that the nitrated musks are non-volatile compounds. The amount of musk represents the complement to 100 by weight of the amount of modifying agent selected.

For obtaining the novel compositions according to the invention, it is possible to proceed in several ways.

According to the simplest embodiment, one proceeds by intimate mixing of the nitrated synthetic musk and the modifying agent utilized in a suitable proportion.

The mixing may be carried out dry, cold or at a temperature above ambient temperature, but preferably not exceeding 80° C.

It is also possible to carry out the mixing in a wet phase, the final composition being consequently dried, for example, by spraying. As a wet medium for the mixing, there may be used a lower alcohol, such as ethyl alcohol or isopropyl alcohol.

According to another feature of the present invention, it is possible to prepare the composition by incorporating the solid modifying agent in the medium wherein the recrystallization of the musk is carried out, the mixing being hence done in situ in the course of the latter. The latter process is found to provide advantageous results with musk xylene.

It is observed that the modifying agents corresponding to the needs of the invention, do not alter the olfactory properties of the musk, while the novel composition has an optimal stability in storage.

The composition according to the invention is applicable in all fields of use of nitrated synthetic musks alone. The most current fields are perfumery products and detergent products. In the formulations intended for perfumery, the novel compositions are incorporated completely and have the same properties as the musk that they contain.

By way of example, a nitrated synthetic musk base composition, such as musk xylene, containing by way of modifying agent, a sugar, such as saccharose, glucose or lactose, their ethers or esters, may be used with success as a fixing agent for fragrance principles in the industry of perfumes, detergents and washing agents.

DESCRIPTION OF PREFERRED EMBODIMENTS

The invention will be now illustrated, without being in any way limited, by the following examples.

EXAMPLE 1

In a double cone mixer of 500 l 150 kg of pure musk xylene in powder or in crystal form and 15 kg of pure glucose are introduced.

It is allowed to rotate for one hour until complete homogenization.

In this way 165 kg are obtained of a composition whose fragrance properties, wettability with water and solution capacities in solvents are identical with those of pure musk xylene.

EXAMPLE 2

The same operational conditions as those described in Example 1 were used, but replacing the glucose by lactose. Identical results were obtained.

EXAMPLE 3

In a heatable double cone 500l mixer capable of being placed under vacuum and containing 92.5% of alcohol and 20 kg of pure powder glucose, 217 kg of musk xylene (derived from recrystallization in isopropyl alcohol) are introduced.

The apparatus is placed under vacuum of 500 mm of mercury and heated to 60° C.

It is allowed to rotate for 2 hours.

In this way 220 kg were obtained of a mixture possessing the properties described in Example 1.

EXAMPLE 4

The same operational conditions as described in Example 3 were used, but replacing the glucose by lactose. Identical results were obtained.

EXAMPLE 5

Examples 1 to 4 above were reproduced replacing the musk xylene by musk ketone and musk ambrette, respectively.

An equivalent result was obtained.

EXAMPLE 6

194 kg of crude musk xylene were dissolved in 600 kg of isopropyl alcohol under reflux. The solution was filtered. Into this solution, 23 kg of pure glucose were added with stirring. The mixture was cooled, still with slow stirring, until complete crystallization of the musk. The crystals were filtered off. After drying, 200 kg were obtained of a mixture having the same properties as that indicated in Example 1.

We claim:

1. In a composition comprising nitrated synthetic musk, the improvement wherein the composition concurrently comprises from 0.5 to 50 percent by weight of a modifying agent; the percentage by weight being based on the total weight of the nitrated synthetic musk and the modifying agent, and said modifying agent being a solid non-filmformer which is at least partially soluble in a lower alcohol, is odorless and is neither toxic nor an irritant to human tissue which it contacts.

2. A composition according to claim 1 comprising from 2 to 20 percent by weight of the modifying agent based on the total weight of the nitrated synthetic musk and the modifying agent.

3. A composition according to claim 1 comprising from 5 to 10 percent by weight of the modifying agent based on the total weight of the nitrated synthetic musk and the modifying agent.

4. A composition according to claim 1, wherein the lower alcohol is ethyl alcohol.

5. A composition according to claim 1, wherein the lower alcohol is isopropyl alcohol.

6. A composition according to claim 1, wherein the modifying agent is a solid which does not substantially change the physical form of the nitrated synthetic musk, and does not interfere with the olfactory properties of the latter.

7. A composition according to claim 1, wherein the modifying agent is, in addition, at least partially soluble in water.

8. A composition according to claim 1 wherein the modifying agent is a sugar, an ether of a sugar or an ester of a sugar.

9. A composition according to claim 8 wherein the sugar is a member selected from the group consisting of maltose, saccharose, glucose, lactose and sucrose.

10. A composition according to claim 1, wherein said modifying agent is saccharose, glucose or lactose.

11. A composition according to claim 1, wherein said modifying agent is a solid hydroxylated product of the polyol type, a paraffins or a solid deodorized hydrocarbon.

12. A composition according to claim 11 wherein the polyols are selected from pentaerythritol and mannitol.

13. A composition according to claim 1 wherein the nitrated synthetic musk is musk xylene.

14. A composition according to claim 1 wherein the nitrated synthetic musk is musk ambrette.

15. A composition according to claim 1 wherein the nitrated synthetic musk is musk ketone.

16. A composition according to claim 1 wherein the nitrated synthetic musk is musk tibetene.

17. A composition according to claim 1 wherein the nitrated synthetic musk is musk moskene.

18. A process for producing a composition according to claim 1 which comprises intimately admixing, as dry materials, the nitrated synthetic musk and the modifying agent.

19. A process according to claim 18 wherein the admixing is effected at a temperature which does not exceed 80° C.

20. A process for producing a composition according to claim 1 which comprises intimately admixing the nitrated synthetic musk with the modifying agent in a lower alcohol and thereafter removing the alcohol from the resulting admixture.

21. A process according to claim 20 which comprises spray drying the resulting admixture to remove the alcohol.

22. A process for producing a composition according to claim 1 which comprises:
  (a) recrystallizing the nitrated synthetic musk in a suitable solvent medium,
  (b) incorporating the solid modifying agent in the solvent medium with said nitrated synthetic musk, and
  (c) admixing said solid modifying agent with the nitrated synthetic musk in situ.

23. A process according to claim 22 wherein said synthetic musk is musk xylene.

24. A commercial product containing a fragrance principle and comprising, as a fixing agent for the fragrance principle, a composition according to claim 1.

25. A perfume according to claim 24.

26. A product according to claim 24 wherein the nitrated synthetic musk is musk xylene and the modifying agent is a sugar.

27. A commercial product containing a fragrance principle and comprising, as a fixing agent for the fragrance principle, a composition according to claim 1 wherein the nitrated synthetic musk is musk xylene and the modifying agent is (a) a sugar selected from the group consisting of saccharose, glucose and lactose, (b) an ester of a sugar selected from the group consisting of saccharose, glucose and lactose or (c) an ether of a sugar selected from the group consisting of saccharose, glucose and lactose.

28. A composition according to claim 1 which consists essentially of the nitrated synthetic musk and the modifying agent.

* * * * *